United States Patent [19]
Drake

[11] Patent Number: 5,118,901
[45] Date of Patent: Jun. 2, 1992

[54] ALKALI METAL AND ALKALI METAL CARBONATE CATALYTIC SYSTEMS AND CATALYTIC PROCESSES

[75] Inventor: Charles A. Drake, Nowata, Okla.

[73] Assignee: Phillips Petroleum Company, Bartlesville, Okla.

[21] Appl. No.: 716,566

[22] Filed: Jun. 17, 1991

Related U.S. Application Data

[62] Division of Ser. No. 583,405, Sep. 17, 1990, Pat. No. 5,063,191.

[51] Int. Cl.$^5$ ................................................ C07C 2/24
[52] U.S. Cl. ........................................ 585/516; 585/500; 585/502; 585/510; 585/520; 585/530
[58] Field of Search ............... 585/500, 502, 520, 530, 585/510, 516

[56] References Cited

U.S. PATENT DOCUMENTS

| | | | |
|---|---|---|---|
| 4,544,790 | 10/1985 | Drake | 585/530 |
| 4,835,330 | 5/1989 | Drake | 585/530 |
| 4,876,410 | 10/1989 | Ewert | 585/530 |
| 4,939,313 | 4/1990 | Drake | 585/530 |

Primary Examiner—Patrick P. Garvin
Assistant Examiner—E. D. Irzinski
Attorney, Agent, or Firm—Carl D. Corvin

[57] ABSTRACT

Catalyst systems containing a catalyst and catalyst support are presented. The catalyst comprises elemental alkali metal and a metal oxide where the metal in the oxide comes from the lanthanide series. Optionally, a promoter is included in the catalyst. The catalyst support comprises an alkali metal carbonate with optionally a carbonaceous compound. This catalyst system can be used to reduce isomerization losses associated with the production of higher alpha-olefins from lower alpha-olefins.

18 Claims, No Drawings

ALKALI METAL AND ALKALI METAL CARBONATE CATALYTIC SYSTEMS AND CATALYTIC PROCESSES

Cross-References to Related Applications

This application is a divisional of U.S. application Ser. No. 07/583,405, filed Sept. 17, 1990 and now U.S. Pat. No. 5,063,191.

BACKGROUND OF THE INVENTION

This invention relates to making an alkali metal and alkali metal carbonate catalytic system. This invention further relates to utilizing the above-mentioned catalytic system to reduce isomerization losses which occur during the production of alpha-olefins.

The production of polymers is a major industry of the United States of America. It has been estimated that the chemical production, in the United States, of a few of the more important plastics and synthetic rubbers, approached forty-five billion pounds, or about twenty billion kilograms, in 1989. These polymers are used in a wide variety of applications. For example, polymers can be used to fabricate such items as pipes, films, fibers, dishes, utensils, automobile parts, beverage containers, and assorted other consumer items.

Polymers, which are basically very long strings of molecules, are made by joining smaller molecules together. These smaller molecules, when used to make polymers, are called monomers. It has also been estimated that the chemical production, in the United States, of a few of the more important monomers, approached seventy-six billion pounds, or about thirty-four billion kilograms, in 1989.

Research has been done to try to make larger monomer type building units in order to facilitate the production of polymers. This research has shown that monomers which have the extra reactivity of a double bond in the first carbon position are generally the preferred monomer choice. The types of monomers are called alpha-olefins to signify that this monomer has a double bond in the first carbon position.

The production of these larger alpha-olefins, which are also called higher alpha-olefins has presented quite a few technical problems. One such problem is the isomerization losses that occur during the production of these higher alpha-olefins. In general, higher alpha-olefins are made from lower alpha-olefins. These lower alpha-olefins are called lower alpha-olefins because they are smaller in size than the higher alpha-olefins they are used to make. Under reaction conditions, these lower alpha-olefins tend to change their structure so that the reactive double bond is no longer attached to the first carbon. This structural change is called isomerization. For example, during a process to produce 3-methyl-1-pentene, which is a higher alpha-olefins, from ethylene and 1-butene, which are lower alpha-olefins, there are isomerization losses of 1-butene. Essentially, 1-butene undergoes a change in structure to 2-butene. This 2-butene is not as reactive as the 1-butene and consequently the 2-butene is not as economically useful. This can be graphically displayed as follows:

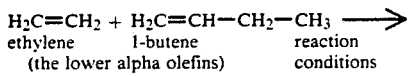

$H_2C=CH_2$ + $H_2C=CH-CH_2-CH_3$ $\xrightarrow{\text{reaction conditions}}$
ethylene    1-butene
(the lower alpha olefins)

$H_2C=CH-CH(CH_3)-CH_2-CH_3$ and
3-methyl-1-pentene
(the intended product-a higher alpha olefin)

$H_3C-CH=CH-CH_3$
2-butene
(unintended byproduct-a non-alpha-olefin)

The above reaction shows that on the 2-butene monomer the double bond is on the inside of the molecule. In contrast, the double bond on the 1-butene monomer is on the front of the molecule. This isomerization of 1-butene to 2-butene produces a significant economic loss. Considering the many different ways that monomers can be used to make polymers, and considering the amount of monomers used to make these polymers, the losses that occur because of isomerization constitute an immense economic loss. These losses are then generally passed on to the consumer of the product.

This invention addresses this economic loss by providing a catalyst system to reduce these losses, the improvement being the addition of a metal oxide to the catalyst wherein the metal oxide comes from the lanthanide series.

SUMMARY OF THE INVENTION

It is an object of this invention to provide an improved catalytic system for the production of higher alpha-olefins.

It is another object of this invention to provide an improved process for the production of higher alpha-olefins.

In accordance with the present invention, a catalytic system comprising a catalyst and a catalyst support, is brought into the presence of a first alpha-olefin having 2 to 10 carbon atoms in the main chain, and a second alpha-olefin having 4 to 10 carbon atoms in the main chain, under conditions suitable to form a higher alpha-olefin. The catalyst comprises an elemental alkali metal and a metal oxide. Furthermore, the metal in the metal oxide is selected from the lanthanide series. The catalyst support comprises an alkali metal carbonate. The term "catalyst support" is not intended in any way to mean that the "catalyst support" is an inert and nonessential component of the catalystic system.

DETAILED DESCRIPTION OF THE INVENTION

I. Alpha-olefin Reactants

Alpha-olefin reactants that are applicable for use in this invention can be divided into two different types.

The first type of alpha-olefin reactants may be characterized as those alpha-olefins which have:

(1) at least one olefinic double bond attached to the first carbon atom; and (2) at least 2 carbon atoms but not more than 10 carbon atoms in the main chain of the molecule; and (3) at least the capability of a homo-coupling reaction (i.e., dimerization) or a hetero-coupling reaction (i.e., co-dimerization), when placed under suitable conditions.

Suitable examples of these types of molecules are ethylene, propylene, 1-butene, 1-pentene, 1-hexene, 1-heptane, 1-octene, 1-nonene, 1-decene, 3-methyl-1-butene, 3-methyl-1-pentene, 5-tert-butyl-1-decene, 4- tert-butyl-7-ethyl-1-decene, 1,4-pentadiene, 1,5-hexadiene, 1,6-heptadiene, 1,7-octadiene, 1,8-nonadiene, 1,9-decadiene, 5-tert-butyl-1,9-decadiene.

The second type of alpha-olefin reactants may be characterized as those alpha-olefins which have:

(1) at least one olefinic double bond attached to the first carbon atom; and (2) at least one allylic hydrogen atom, i.e., a hydrogen atom attached to a carbon atom where that carbon atom is attached and adjacent to a double-bonded carbon atom; and (3) at least four but not more than 10 carbon atoms in the main chain of the molecule; and (4) at least the capability of a homo-coupling reaction (i.e., dimerization) or a hetero-coupling reaction (i.e., co-dimerization), under suitable conditions.

Suitable examples of these types of molecules are 1-butene, 1-pentene, 1-hexene, 1-heptene, 1-octene, 1-nonene, 1-decene, 3-methyl-1-butene, 3-methyl-1-pentene, 5-tert-butyl-1-decene, 4-tert-butyl-7-ethyl-1-decene, 1,4-pentadiene, 1,5-hexadine, 1,6-heptadiene, 1,7-octadiene, 1,8-nonadiene, 1,9-decadiene, 5-tert-butyl-1,9-decadiene.

It should be noted that this invention does not apply to reactions of ethylene with ethylene, ethylene with propylene, or propylene with propylene, because these reactants do not undergo undesirable isomerization reactions.

II. Catalytic System

Catalyst

Elemental Alkali Metal

The alkali metals contemplated to be within the scope of the invention include lithium, sodium, potassium, rubidium and cesium. While the proportion of the alkali metal combined with the alkali metal carbonate support can vary appreciably, generally at least about one weight percent of alkali metal based on the total weight of the support will be employed. Generally, about 1 to about 20 weight percent alkali metal will be employed with about 2 to about 15 weight percent preferred. An alkali metal loading of about 3 to about 10 weight percent based on the total weight of the support is most preferred. In general when selecting the amount of elemental alkali metal to use the factors to consider are: the desired catalytic activity; the desired selectivity of the catalytic system; the ease in preparing the catalyst; the most efficient use of the reagents; and the economic factors associated with making the catalyst.

Metal Oxides

The metal oxides contemplated to be within the scope of the invention include those metal oxides of the Lanthanide series. In particular they are cerium (III) oxide, praseodymium (III) oxice, neodymium (III) oxide, samarium (III) oxide, europium (III) oxide, gadolinium (III) oxide, terbium (III) oxide, dysposium (III) oxide, holium (III) oxide, erbium (III) oxide, thulium (III) oxide, ytterbium (II) oxide, lutetium (III) oxide. In general, the amount of metal oxide to be added is from about 0.1 to about 10 weight percent. More preferably, the amount added is from about 0.5 to 5 weight percent, and most preferablly from about 0.7 to about 3 weight percent where all the weight percents are based on the total weight of the catalyst support. An amount of 0.7 to 3 weight percent is preferred because of economic and processing factors. Generally, cerium (III) oxide is the preferred metal oxide of choice due to its availability and ease of use.

Optional Catalyst Components

Optionally, the catalyst can include one or more of the following promoters: elemental copper; elemental cobalt; finely divided stainless steel; and finely divided glass. The proportion of optional promoter than can be added varies by a considerable amount, but generally, at least one weight percent of the optional promoters(s) based on the total weight of the support can be added to the catalyst. The following amounts are provided for additional guidance:

| Promoter | Loading Weight Percent | | |
|---|---|---|---|
| | Broad | Intermediate | Preferred |
| Cu | 1–30 | 3–20 | 5–12 |
| Cu | 1–50 | 3–25 | 5–15 |
| *SS | 1–80 | 3–60 | 5–50 |
| Glass | 1–50 | 2–25 | 3–15 |

It should be noted, that the catalyst system of the invention can contain addditional components which do not adversely affect the catalyst performance, such as pigments, dyes, processing aids, inert fillers, binders, or mixtures of these similar components.

Catalyst Support

Alkali Metal Carbonate

Any suitable alkali metal carbonate can be used in the preparation of the catalsyt support. Examples of suitable alkali metal carbonates include lithium carbonate, sodium carbonate, potassium carbonate, rubidium carbonate, and cesium carbonate as well as mixtures of these carbonate. In general, potassium carbonate is used due to its availability on the commercial market.

Optional Catalyst Support Components

The alkali metal carbonate support can optionally contain at least one carbonaceous compound. For purposes of this disclosure, the term "carbonaceous compound" is intended to include various forms of the element carbon, including, but not limited to, carbon black, charcoal, coconut charcoal, amorphous graphite, crystallite graphite, and the like, as well as mixtures of any two or more thereof. Finely divided graphite is presently preferred because it is useful both as a die lubricant for the pelleting process and it imparts improved activity to the finished catalyst system. The carbonaceous compound, if employed, comprises from about 0.1 to about 20 weight percent of the total alkali metal carbonate support. Preferably, the carbonaceous compound comprises about 0.3 to about 5 weight percent of the support. In general, factors to consider in determining the amount of carbonaceous compound to add are, the methods used in processing the support, the availability of the components for the support, and the cost of the components.

III. Preparation of the Catalyst Support

It is known in the art how to prepare an alkali metal carbonate support by making a thick paste in water and eventually forming a pelletized, tabletted, or granular support. For example, commercially available alkali metal carbonate, in the form of powder, granules, or the like, can be mixed with just enough water to form a thick paste as known in the art. this thick paste can then be formed into a particulate product prior to calcining. This paste can then be formed into an extrudate using an extruder. This extrudate can be any diameter, but for best catalytic activity, ease of handling, and processability, the extrudate is from about 1/16 to about ¼ inch in diameter. After the extrudate passes through a die, the extrudate can be cut into uniform lengths, if desired. Howver, uniform lengths are not always necessary, so the extrudate can be allowed to break on its own, into any length of abut 2 to about 7 times the diameter's width. Usually, the extrudate is allowed to break of its own accord for easy manufacturing.

The thick paste after drying and granulation can also be formed into tablets using a die press, a punch press, or a pelleting machine. Tablets are usually very uniform in size. Tablets look similar to an extrudate, except the two ends of each cylindrical tablet are convex, not blunt.

Another method of forming a particulate product from the thick paste is to oven dry the thick paste under conditions of time and temperature sufficient to insure that substantially all of the water is driven off. The dried paste can then be broken into pieces and fractionated by suitable means such as by passing the paste through the desired screen size and recovering a certain particle fraction.

After formation of the support, it should be dried under conditions of time and temperature sufficient so that substantially all of the water is driven off. Usually, a temperature in the range of about 80° to about 350° C., preferably a temperature in the range of about 85° to about 150° C., for at least 2 hours is sufficient. Drying can occur under any atmosphere, but for safety reasons, a vacuum oven is usually employed.

Once the catalyst support is formed and dried, it should be calcined in an oxygen-containing atmosphere at a temperature in the range of about 80° to about 350° C., preferably about 250° C., for at time of at least 2 hours. Upon completion of calcination, the catalyst support can be stored in a dry atmosphere. Preferably, the catalyst support is stored under a dry, oxygen-free atmosphere until needed for further treatment.

IV. Preparation of the Catalyst System

The general procedure for preparation of the catalyst system after calcining the support, involves heating the alkali metal carbonate support to a temperature in the range of about 80° to about 350° C. Preferably the temperature is slightly above the melting point of the particular elemental alkali metal used. The catalyst support is then cooled and contacted with at least one elemental alkali metal and at least one metal oxide from the lanthanide series, in a dry, oxygen-free atmosphere. The temperature should be sufficient to cause the added elemental alkali metal to melt. The contacting, which is done in an oxygen-free atmosphere, is preferably carried out with suitable mixing to ensure an even distribution of the catalyst components. Suitable temperatures for the contacting step will vary with the particular elemental alkali metal employed. For example, with elemental potassium, temperatures in the range of about 80° to 100° C. are preferred, while with elemental sodium, temperatures in the range of about 100° to 140° C. are preferred.

While the support is maintained at or above the melting point of the particular elemental alkali metal used, in an oxygen-free atmosphere, any desired promoter(s), such as finely divided stainless steel or elemental copper, can be gradually added while the treated catalyst is continuously stirred. For example, with potassium, temperatures in the range of about 80° to about 100° C. are employed. The catalyst system is then ready to be charged to the reactor.

Optionally, the alkali metal carbonate support, once elemental alkali metal, metal oxide, and any desired promoters have been deposited thereon, can be subjected to a subsequent heating step, in an oxygen-free atmosphere, to ensure as uniform a distribution as possible, of the various components, on the surface of the alkali metal carbonate support. Thus, the finished catalyst can be subjected to a temperature of at least 80° C. for a time in the range of about 0.1 to 4 hours. A temperature in the range of about 150° to about 250° C. for a time in the range of about 0.5–2 hours is presently preferred for the most uniform distribution.

Optionally, prior to charging the reactor, the catalyst system can be mixed with an inert substance to dilute the catalyst system and decrease the rate of the alpha-olefin reaction. Any inert substance which has no catalytic activity in an alpha-olefin reaction can be used. One example of such an inert substance is glass beads.

As indicated by the variety of supports, alkali metal components, metal oxides, and promoters included within the scope of the invention, numerous catalyst system combinations are possible. Any combination of the alkali metal, metal oxide, and optional promoters disclosed can be supported on any alkali metal carbonate support disclosed. The combination of alkali metal carbonate, elemental alkali metal, and metal oxide which one may choose to employ will depend on a variety of variables such as reactor configuration, reaction temperature and pressure, alpha-olefin feed employed, rate of alpha-olefin feed, and conversions desired.

V. Employment of the Catalyst System Under Reaction Conditions

The reaction of the invention can be carried out using either batch or continuous types of operation, although the catalyst system of this invention are particularly well suited for continuous, fixed bed, operation. Suitable equipment such as autoclaves, tubular reactors, or similar equipment are well known in the art and can be employed. No special materials of construction are required consequently, steel, stainless steel, and glass-lined reactors can be employed.

The reaction temperature can vary depending on the catalyst system and type of feed(s) employed. Typically, a temperature in the range of about 50° to about 250° C. is suitable. Temperatures of about 80° to about 200° C. are preferred with a range of about 100° to about 170° C. most preferred because optimum reaction rates are obtained with minimum by-product formation.

The reaction can be carried out by contacting the alpha-olefins with the catalyst system in the liquid phase or the gas phase, depending on the structure and molecular weight of the alpha-olefin, as well as reaction temperature and pressure employed. Pressure during the reaction can vary between wide limits. In general, higher pressures favor the progress of the reaction. Thus, pressures of atmospheric up to about 10,000 psig and higher are suitable. Preferably, pressures of about 100 to 5,000 psig are employed, with pressure of about 1,000 to about 4,000 psig most preferred in order to achieve a good balance between reaction rates and costs necessitated by very high reaction pressures.

If the reaction is carried out in the liquid phase, solvents or diluents such as pentane, hexane, cyclohexane, and dodecane are suitable. If the reaction is carried out in the gaseous phase, diluents such as methane and ethane are suitable. Furthermore, substantially inert gases such as nitrogen and argon can be used alone or in conjunction with these hydrocarbons as gas phase diluents.

The contact time required for the reaction depends upon several factors such as the temperature, pressure, activity of the catalyst system, structure of the reactants employed, and the level of conversion desired. The length of time during which the alpha-olefinic compounds are contacted with the catalyst system can vary conveniently between about 0.1 seconds and about 24 hours although shorter and longer contact times can be employed. Where the reaction is carried out in continuous fashion, it is convenient to express the reactant/catalyst system contact time in terms of weight hourly space velocity (WHSV), i.e., the ratio of the weight of reactant which comes in contact with a given weight of catalyst system per unit time. Thus, a WHSV of about 0.1 to about 10 can be employed. A WHSV of about 0.5 to about 5 is preferred, with about 1 to about 4 WHSV most preferred for optimum catalyst system productivity.

EXAMPLE

The catalyst support, in this example, was prepared in accordance with this specification and accepted practice in the art. See for example Ewert et al., U.S. Pat. No. 4,810,688 and Drake U.S. Pat. No. 4,895,819 as additional references. Specifically, the catalyst support was prepared from commercially available anhydrous potassium carbonate and deionized water. Sufficient water was added to the solid particles to form a thick paste. Usually, about 2 milliters of water were added to about 1 gram of solid material. The thick paste was thoroughly mixed and then dried at about 85° C. in a vacuum oven for at least two hours in the presence of air. The dried paste was then calcined at about 250° C. for 3 hours in an oxygen containing atmosphere. The support was then allowed to cool at 85° C., in an oxygen free atmosphere. After reaching 85° C., elemental potassium and stainless steel was added to the support. The amount of elemental potassium added was 8 weight percent based on the catalyst support weight. The amount of stainless steel added was 5 weight percent based on the catalyst support weight. In run number 5, one weight percent of cerium (III) oxide was also added to the catalyst. To insure an even distribution of catalyst on the catalyst support the catalyst system was heated to 230° C. for one hour.

In each of the following runs the codimerization of ethylene with 1-butene was carried out in a steam heated 316 stainless steel tubular reactor (⅜"×20"). The catalyst system (27 grams; density about 0.84 g/ml), was combined with 25 grams of inert substance to dilute the catalyst system and control the reaction rate. The contents of the tubular reactor was heated to reaction temperature of about 100° to 120° C. After about 6 hours the unreacted monomer solution was analyzed for its content. The following data were collected:

| Run | 1-Butene Ethylene wt percent | Temperature °C. | % K | % SS | % $Ce_2O_3$ | 1-Butene 2-Butene ratio |
|---|---|---|---|---|---|---|
| | | | weight percent in the catalyst | | | |
| 1 | 4:1 | 120 | 8 | 5 | 0 | 2.5 |
| 2 | 4:1 | 100 | 8 | 5 | 0 | 4.5 |
| 3 | 3:1 | 100 | 8 | 5 | 0 | 5.2 |
| 4 | 3:1 | 100 | 8 | 5 | 0 | 3.4 |
| 5 | 3:1 | 100 | 8 | 5 | 0 | 18 |

It is apparent from the above data that the addition of a small amount of cerium (III) oxide reduced the losses due to isomerization of 1-butene to 2-butene significantly. Indeed, the ratio of 1-butene to 2-butene was increased about 30 percent.

While this invention has been described in detail for the purpose of illustration, it is not to be construed as limited thereby, but is intended to cover all changes and modifications within the spirit and scope thereof.

That which is claimed is:

1. A process for producing higher alpha-olefins which comprises:
    contacting, under suitable conditions, a first alpha-olefin containing 2 to 10 carbon atoms in the main chain, with a second alpha-olefin containing 4 to 10 carbon atoms in the main chain, in the presence of a catalytic system comprising:
    a catalyst which comprises an elemental alkali metal and a metal oxide wherein the metal is chosen from the lanthanide series; and a catalyst support which comprises an alkali metal carbonate.

2. A process according to claim 1 wherein said first alpha-olefin is selected from the group consisting of ethylene, propylene, 1-butene, 1-pentene, 1-hexene, 1-heptene, 1-octene, 1-nonene, 1-decene, or mixtures thereof.

3. A process according to claim 1 wherein said first alpha-olefin is ethylene.

4. A process according to claim 1 wherein said second alpha-olefin is selected from the group consisting of 1-butene, 1-pentene, 1-octene, 1-nonene, 1-decene, or mixtures thereof.

5. A process according to claim 1 wherein said second alpha-olefin is 1-butene.

6. A process according to claim 1 wherein said elemental alkali metal is selected from the group consisting of lithium, sodium, potassium, rubidium, cesium, or mixtures thereof.

7. A process according to claim 1 wherein said elemental alkali metal is potassium.

8. A process according to claim 1 wherein the concentration of said elemental alkali metal in said catalyst is in the range of about 1 to about 20 weight percent based on the total weight of said catalyst support.

9. A process according to claim 1 wherein said metal oxide is selected from the group consisting of cerium (III) oxide, praseodymium (III) oxide, neodymium (III) oxide, samarium (III) oxide, europium (III) oxide, gadolinium (III) oxide, terbium (III) oxide, dysprosium (III) oxide, holium (III) oxide, erbium (III) oxide, thulium (III) oxide, ytterbium (III) oxide, lutetium (III) oxide, or mixtures thereof.

10. A process according to claim 1 wherein said metal oxide is cerium (III) oxide.

11. A process according to claim 1 wherein the concentration of said metal oxide in said catalyst is in the range of about 0.1 to about 10 weight percent based on the total weight of said catalyst support.

12. A process according to claim 1 wherein said alkali metal carbonate is selected from the group consisting of lithium carbonate, sodium carbonate, potassium carbonate, rubidium carbonate, cesium carbonate, or mixtures thereof.

13. A process according to claim 1 wherein said alkali metal carbonate is potassium carbonate.

14. A process according to claim 1 wherein said catalyst further comprises a promoter selected from the group consisting of elemental copper, elemental cobalt, finely divided stainless steel, finely divided glass, or mixtures thereof.

15. A process according to claim 1 wherein said catalyst further comprises finely divided stainless steel.

16. A process according to claim 1 wherein said catalyst support further comprises a carbonaceous compound selected from the group consisting of carbon black, charcoal, coconut charcoal, amorphous graphite, crystallite graphite, or mixtures thereof.

17. A process to produce 3-methyl-1-pentene which comprises:

contacting, at a temperature in the range of about 50° C. to about 250° C. and a pressure in the range of about atmospheric to about 10,0000 psig, ethylene with 1-butene, in the presence of a catalytic system comprising, a catalyst which comprises, elemental potassium and cerium (III) oxide, and a catalyst support which comprises potassium carbonate said elemental potassium being present in an amount in the range of about 1 to about 20 weight percent based on the weight of said support and said cerium (III) oxide being present in an amount in the range of 0.1 to 10 weight percent based on the weight of said support.

18. A process according to claim 17 wherein said temperature is in the range of 100° C.–170° C. and said pressure is in the range of 1,000 to 4,000 psig.

* * * * *